US00PP09951P

United States Patent [19]

Fruehwirth

[11] Patent Number: Plant 9,951

[45] Date of Patent: Jul. 8, 1997

[54] POINSETTIA PLANT NAMED '725'

[75] Inventor: Franz Fruehwirth, Encinitas, Calif.

[73] Assignee: Paul Ecke Ranch, Inc., Encinitas, Calif.

[21] Appl. No.: 621,001

[22] Filed: Mar. 22, 1996

[51] Int. Cl.[6] ..... A01H 5/00

[52] U.S. Cl. ..... Plt./86.4

[58] Field of Search ..... Plt./86.4

*Primary Examiner*—Howard J. Locker

*Attorney, Agent, or Firm*—Arnold, White & Durkee

[57] ABSTRACT

Poinsettia '725' is a new cultivar, distinguished by dark red flower bracts, dark green foliage, self-branching characteristics, uniform growth habit and 9-week flowering response time. The new plant produces a very desirable branched flowering pot plant for the mid-season holiday market. Poinsettia '725' is resistant to epinasty after being confined to shipping containers. The post-production foliage and bract retention are excellent even under low light intensities in the consumer's home.

2 Drawing Sheets

BACKGROUND OF THE NEW PLANT

This new poinsettia cultivar, '725', originated as an induced self-branching sport of a seedling known as 'M-06' (not patented) in my green house in Encinitas, Calif. It was selected because of its dark, rich red flower bracts, dark green foliage, self branching characteristics, and uniform growth habit; traits that distinguish it from other poinsettia cultivars, and seem to make it a desirable plant for commercial greenhouse production. After selection, '725' was vegetatively reproduced from stem cuttings for test purposes in Encinitas, Calif. 'M-06' is a proprietary plant and there are no specimens in the public domain. Poinsettia 'M-06' is not self-branching in that no axillary branches develop as long as the apical bud is not removed (pinched). '725' is self-branching in that during development axillary branches elongate without removal of the apical bud. Under short day conditions, the axillary branches will develop flowers.

Poinsettia '725' most closely resembles poinsettia '140' (U.S. Plt. Pat. No. 7,874), but differs in these aspects: '725' has a more uniform growth habit, more cyathia, smoother flower bracts and flowers later than '140' under the same cultural conditions. Subjecting clones of this plant to successive generations of vegetative propagation, it was demonstrated that the distinctive characteristics of '725' held true from generation to generation.

DESCRIPTION OF THE PHOTOGRAPHS

Poinsettia '725' is illustrated in the accompanying color photographs.

DESCRIPTION OF THE PLANT

Figure 1:
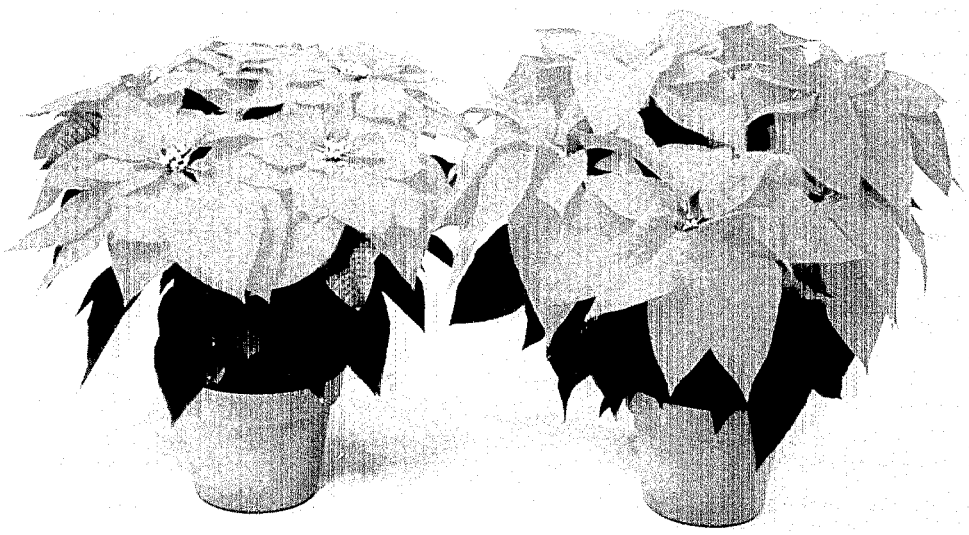
FIG. 1 is a side view of a branched '725' plant, left, compared to another dark leafed cultivar '140', right, in full flower.
Figure 2:
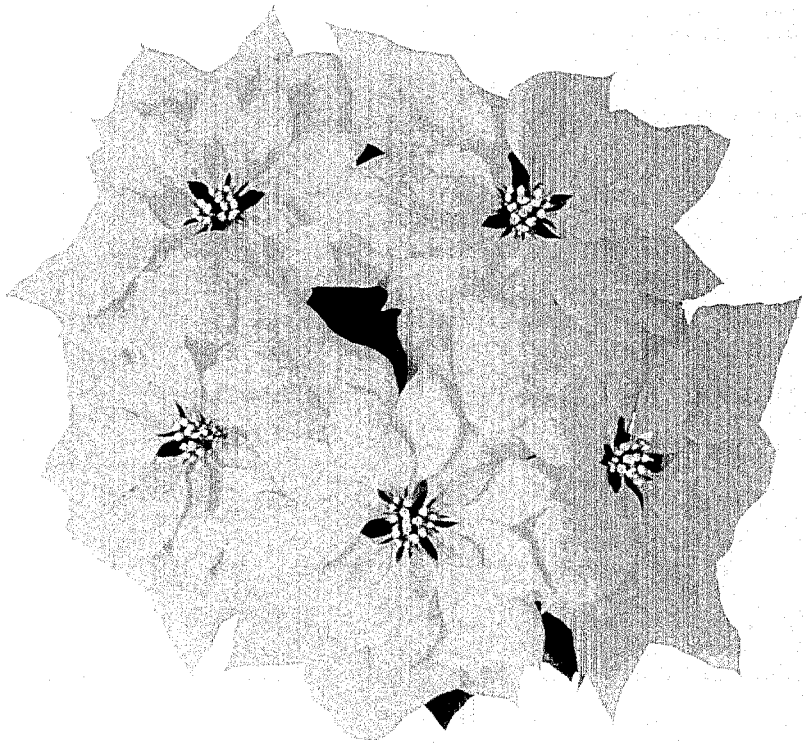
FIG. 2 is a top view of the same '725' plant showing flower and bract formation.

The following is a detailed description of this new poinsettia as observed in Encinitas, Calif., USA during December 1994. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between Poinsettia '725'; and the plant is most closely resembles, Poinsettia '140' (U.S. Plant Pat. No. 7,874) under the same cultural conditions.

| Plant | '725' | '140' |
|---|---|---|
| Flowering response | 9 weeks | 8 weeks |
| No. of Bracts | 16–18 | 10–12 |
| Bract color | RHS 45A-B | RHS 46A-B |
| No. of cyathia | 14–15 | 8–10 |

Origin: Sport of a seedling. The sport was induced by application of the procedures set forth in U.S. Pat. No. 4,724,276, incorporated by reference in its entirety, to the seedling plant. Root stock used as 'Angelika' (U.S. Plant Pat. No. 5,492).

Classification:

*Botanical.*—*Euphoribia pulcherrima* Willd.

*Common name.*—Poinsettia.

*Cultivar name.*—'725'.

Form: Shrub.

Height: Short–medium.

Growth habit: Single stemmed plant, upright and vigorous with self-branching side shoots. The application of a chemical growth retardant may not be needed to restrict height for commercial pot plant production. I observed a branched plant in a pot with an overall height of 38 cm and an overall width of 45 cm. The bract diameter of inidividual flowers was 24 cm.

Branching: Axillary branches will develop and terminate in a flower without pinching. However, it is usually desirable to pinch '725' before flower induction and remove all terminal dominance. Then, all axillary branches will develop uniformly and at a faster rate.

Growth rate: Rooting of stem cutting occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The leaves are of medium size, leaf blades typically 12 cm long and 8 cm wide with leaf petiols 6 cm long and deep red. The upper leaf surface is glabrous and the under surface is finely pubescent.

*Leaf shape.*—Typical leaves are generally ovate with obtuse bases and acuminate tips. Leaf margins are mostly entire but some with 1 or 2 indentations on each side of the leaf blade.

*Color.*—Upper side — Rich, dark red, between. R.H.S. 147A. Under side — Green, R.H.S. 174A-B.

*Retention.*—The foliage lasts extremely well even under low light intensities in the consumer's home.

Bracts: Generally there are 16–18 rich red bracts of various sizes subtending the cyathia. The primary bracts have blades typically 13–14 cm long and 8–9 cm wide with petioles 2–3 cm long.

*Shape.*—Primary bracts are ovate with acute bases and acuminate tips. Primary bract margins are entire or occasionally lobed with 1 or 2 indentations on either side of the bract. Secondary bracts are of various sizes, obovate to elliptical, and have entire margins.

*Color.*—Upper side — Rich, dark red, between. R.H.S. 45A-B. Under side — Red, near R.H.S. 47A.

Flowers: Generally, 14–15 cyathia (flowers) are present when the plant is in full bloom. Each cyathium is about 6 mm long and 5 mm wide, green in color, and fringed with red at the distal end. A yellow nectar cup protrudes from the side of each cyathium. The flower pedicel is also green and about 5 mm in length. The stamens protruding from the cyathia are dark red. The anthers are bifurcate; the pollen is yellow and copious. The stigmas are dark red and trifurcate.

*Nectar exudate.*—Abundant.

*Seeds.*—Self-incompatible

*Fertility.*—Not observed.

Post production: Poinsettia '725' is resistant to epinasty after being confined to shipping containers and retains its leaves and flower bracts for several weeks in the consumer's home environment.

What is claimed is:

1. A new and distinct cultivar of Poinsettia plant, substantially as herein shown and described, distinguished by its dark red flower bracts, dark green foliage, self-branching characteristics and uniform growth habit.

* * * * *